United States Patent
Lent et al.

(10) Patent No.: US 6,458,118 B1
(45) Date of Patent: Oct. 1, 2002

(54) DRUG DELIVERY THROUGH MICROENCAPSULATION

(75) Inventors: Mark S. Lent, Brooklyn Park; Kenneth T. Heruth, Edina; Thomas R. Prentice, Lake Elmo, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/511,438

(22) Filed: Feb. 23, 2000

(51) Int. Cl.[7] ................................................ A61K 9/22
(52) U.S. Cl. ........................ 604/891.1; 604/890.1; 604/288.01; 604/288.04; 604/288.02
(58) Field of Search ............... 604/890.1, 891.1, 604/892.1, 288.01, 288.02, 288.03, 288.04, 22, 500, 502

(56) References Cited

U.S. PATENT DOCUMENTS

| | | | |
|---|---|---|---|
| 3,527,220 A | * 9/1970 | Summers | 128/260 |
| 3,915,393 A | * 10/1975 | Elkins | 241/168 |
| 4,003,379 A | 1/1977 | Ellinwood, Jr. | |
| 4,692,147 A | 9/1987 | Duggan | |
| 5,059,175 A | * 10/1991 | Hanover et al. | 604/891.1 |
| 5,085,644 A | * 2/1992 | Watson et al. | 604/891.1 |
| 5,106,627 A | 4/1992 | Aebischer et al. | |
| 5,366,454 A | * 11/1994 | Currie et al. | 604/891.1 |
| 5,382,236 A | * 1/1995 | Otto et al. | 604/891.1 |
| 5,462,525 A | 10/1995 | Srisathapat et al. | |
| 5,466,465 A | * 11/1995 | Royds et al. | 424/449 |
| 5,476,460 A | * 12/1995 | Montalvo | 604/891.1 |
| 5,480,656 A | * 1/1996 | Okada et al. | 604/891.1 |
| 5,639,275 A | 6/1997 | Baetge et al. | |
| 5,643,207 A | * 7/1997 | Rise | 604/890.1 |
| 5,711,316 A | 1/1998 | Elsberry et al. | |
| 5,895,372 A | * 4/1999 | Zenner et al. | 604/890.1 |
| 6,198,966 B1 | * 3/2001 | Heruth | 604/891.1 |
| 6,305,378 B1 | * 10/2001 | Lesh | 128/898 |

* cited by examiner

Primary Examiner—Ira S. Lazarus
Assistant Examiner—Tu Cam Nguyen
(74) Attorney, Agent, or Firm—Banner & Witcoff, Ltd.

(57) ABSTRACT

An implantable drug delivery device comprising a microencapsulated drug contained within at least one capsule, a carrier fluid that will dissolve the drug when freed from the capsule, a drug releaser for freeing the microencapsulated drug from the capsule, a reservoir in which the carrier fluid dissolves the drug, and an electromechanical pump to convey the dissolved drug to a catheter, through which the drug is delivered to a target site within a patient.

34 Claims, 3 Drawing Sheets

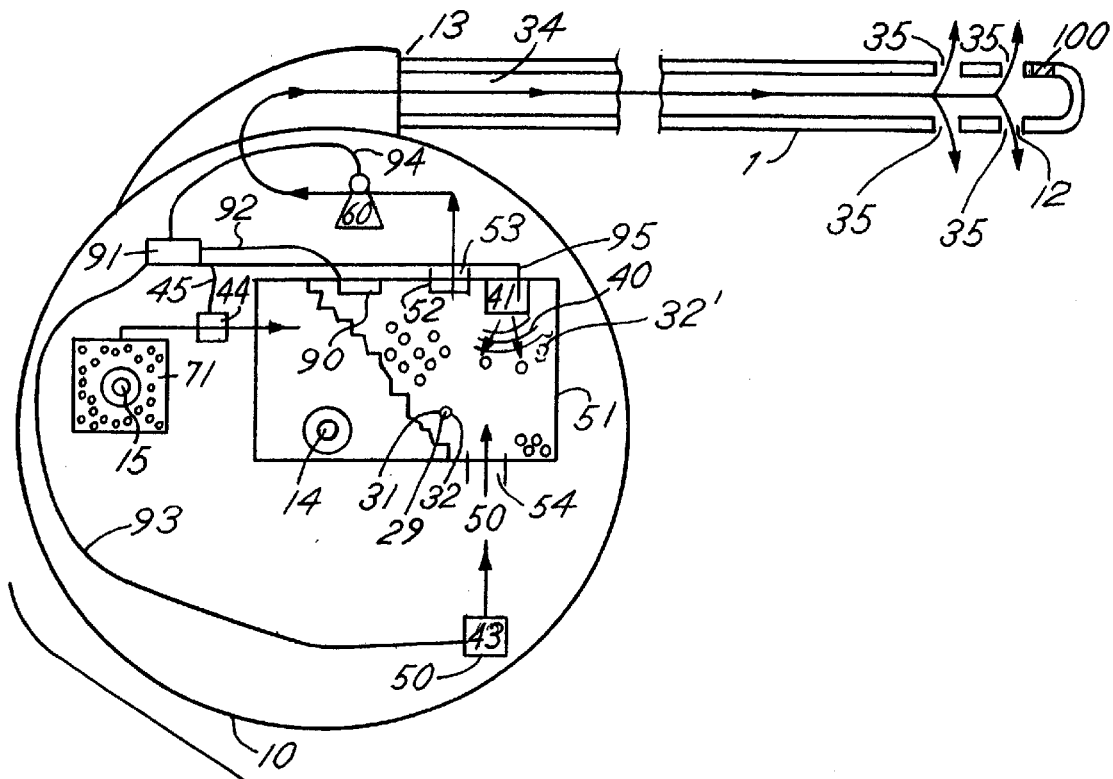
FIG.3
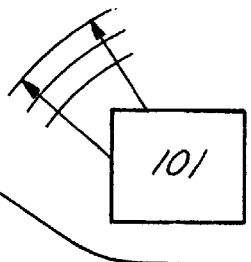
FIG.4
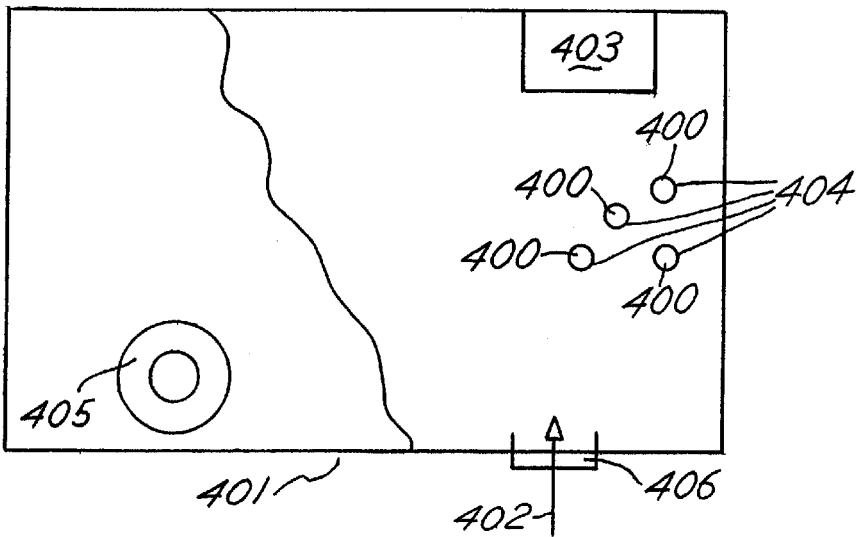

DRUG DELIVERY THROUGH MICROENCAPSULATION

BACKGROUND OF THE INVENTION

1. Field of the Invention

This invention relates to drug delivery techniques, and more particularly relates to such techniques for treating neurodegenerative disorders.

2. Description of Related Art

There are a number of conventional apparatuses and methods for drug delivery to a patient. Implanted drug delivery systems have involved two general approaches. One approach is to use an implanted drug administration device, wherein drugs are pumped from a reservoir to a target site within a patient. See e.g., U.S. Pat. Nos. 5,711,316; 4,692,147; 5,462,525; and 4,003,379. The reservoir can be replenished as necessary through a replenishing port, and without removal of the implanted device from the patient. Some drugs are not stable when dissolved in a vehicle delivery solvent. Other drugs are stable for only a short period of time when dissolved in a solvent. Some drugs are stable for example for only 30 to 90 days. After that time, the drug will precipitate out of solution, or the drug molecule may be altered. When a significant amount of the drug has degraded, the solution has to replaced, even if a useful quantity is still available in the reservoir. When this occurs, the patient must visit a medical center to have the reservoir emptied of the degraded solution and refilled with non-degraded solution.

Most conventional devices store the drug to be delivered in a reservoir, with the drug dissolved in a liquid solvent, such as water or saline. The stored solution is quite dilute, e.g. 1–5% of the drug compared to 95–99% carrier. Further, the reservoir in the device for the delivered drug must be large enough for the requisite solvent, and the reservoir must be replenished frequently. Thus, there is a need for devices and methods that can deliver drugs that are not stable when dissolved in a solvent, and to do so in a controlled manner. There is also a need for smaller devices that do not have the large reservoir required by conventional devices and methods.

A second approach has been to use implanted capsules that will permit the drug within the capsule to transfer outside of the capsule wall by diffusion and/or by the dissolving of the capsule wall. See e.g., U.S. Pat. Nos. 5,106,627 and 5,639,275. A major drawback with this approach is that it is a passive drug delivery system that drug delivery cannot be controlled after implantation of the capsule within the patient. Further, additional capsules must be implanted after earlier capsules are dissolved or spent.

In addition, conventional sensing systems are limited due to the fact that certain substances are not directly measurable using conventional sensors. In these circumstances, the substance must be reacted with a reagent to produce a substance that can be directly measured using conventional sensors. As an example, oxygen can but glucose cannot be directly measured by conventional sensors, so an oxidase is reacted with glucose to produce oxygen, the level of which is then directly measured by the sensor and which corresponds to the level of glucose at the target site. A conventional manner for providing reagent to produce a measurable substance is one that has a set amount of initial reagent within a disposable sensor. A drawback of this conventional approach is that the reagent is consumed and there is no way to replenish the consumed reagent short of removing the disposable sensor and replacing it with a new disposable sensor containing reagent. Alternative methods for providing a sufficient amount of reagent to produce the directly measurable substance are desirable, particularly to extend the useful life of a sensor.

The present invention is directed to these difficulties which the prior art fails to address.

SUMMARY OF THE INVENTION

A preferred form of the invention can provide controlled drug delivery. The drug is stored within an implantable device in solid form. Small amounts of the drug, e.g. 1 microgram, are encapsulated in an inert material, e.g. a stable polymer. The encapsulated drug is stored in a reservoir of the implantable device. Further, there may be a supply of pure carrier in the implantable infusion device. This can be a separate carrier, such as water, stored in a separate reservoir system. In addition, the supply of pure carrier can be replenished.

The carrier can also be a body fluid, such as cerebrospinal fluid from the patient's body. This concept of dissolving a drug into a stream of recirculating body fluid is disclosed in U.S. Pat. No. 5,643,207, which is incorporated herein by reference.

When drug infusion is desired, some of the encapsulated drug is metered by the implantable device into the carrier fluid. The capsules are broken, thereby freeing the drug to be dissolved in the carrier fluid within the device. The carrier fluid with the dissolved drug is then infused by an electromechanical pump of the device to the target site within the patient.

The capsules can be broken in any suitable manner by a drug releaser involving any suitable mechanism, including: ultrasonic waves, mechanical crushing or grinding; chemically dissolving or splitting; applying an electrical current to potentiate a chemical reaction; heating; or applying pressure (e.g. hydrostatic pressure). Thus, in accordance with the present invention, the drug releaser can comprise, by way of example, an ultrasonic sound emitter, a mechanical crushing or grinding device, a chemical dissolving or chemical splitting apparatus, an electrical current emitter, a heater, or a pressure device.

It is an objective of the present invention to provide implantable devices and methods for drug delivery that are smaller than conventional devices and methods.

It is a further objective of the present invention to provide implantable devices and methods for drug delivery for longer periods of time without replenishing than is required for conventional devices and methods.

It is a further objective of the present invention to provide implantable devices and methods for delivery of drugs that are not stable when dissolved in a fluid.

It is a further objective of the present invention to provide alternative methods to replenish reagents required for chemical reactions to produce substances that can be directly measured using conventional sensors, as well as to extend sensor life.

Those of skill in the art will recognize these and other benefits that the above apparatus and methods provide over conventional devices.

BRIEF DESCRIPTION OF THE DRAWINGS

FIG. 3 is a diagrammatic illustration of another preferred embodiment of the implantable drug delivery device of the present invention, including an electromechanical pump, reservoir, microencapsulated drug in a premixing vessel, and a catheter.

FIG. 4 is a diagrammatic illustration of another preferred embodiment of the invention having a supply of microencapsulated reagent that when freed from the capsule can react with a first substance to produce a second substance that can be measured by conventional sensors.

DESCRIPTION OF THE PREFERRED EMBODIMENTS

Figure 1A:
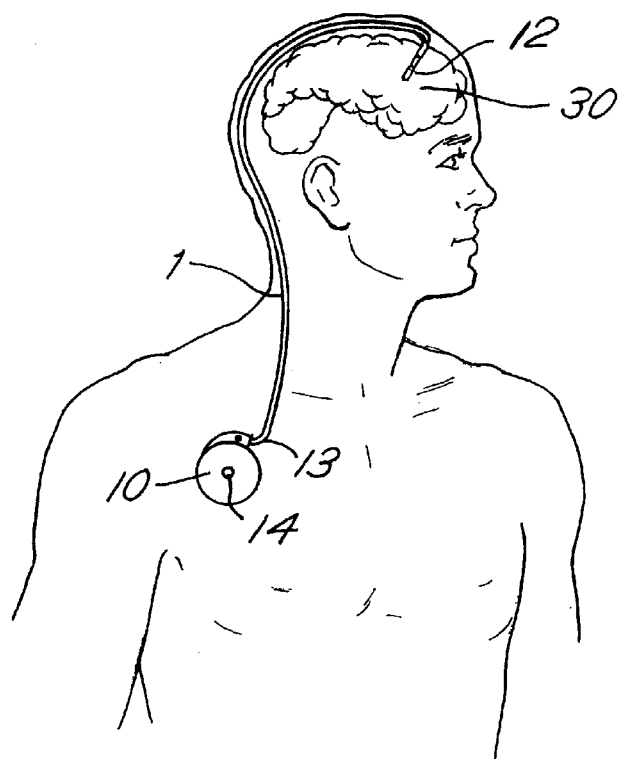
FIGS. 1A and 1B are diagrammatic illustrations of the present invention implanted in a patient.
Figure 1B:
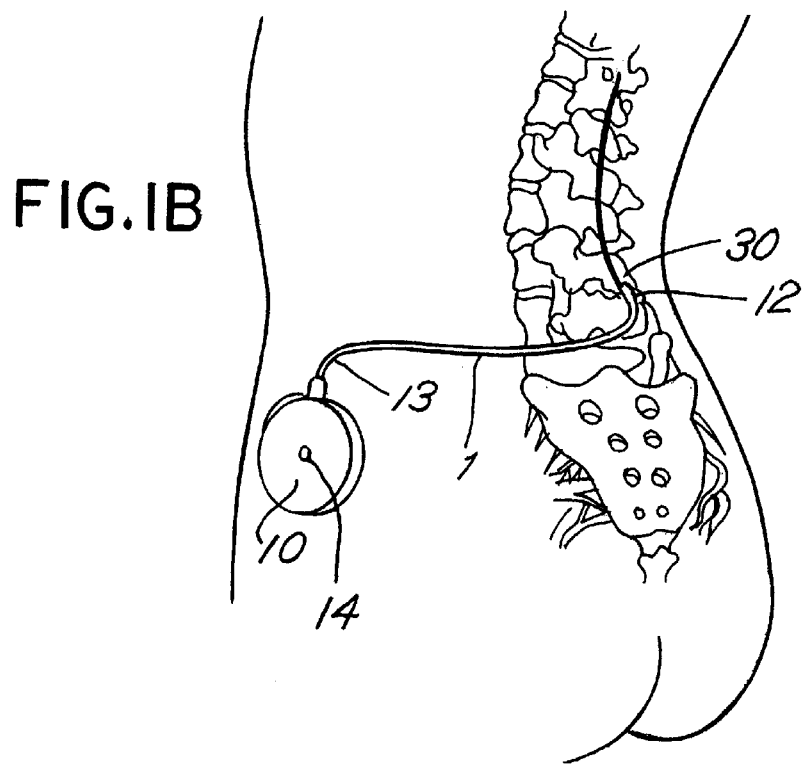

Referring to FIGS. 1A and 1B, an implantable system or device 10 made in accordance with the preferred embodiment may be implanted below the skin of a patient. The implantable device 10 has a port 14 into which a hypodermic needle can be inserted through the skin to inject a quantity of microcapsules 31 containing a medication or drug 29. Catheter 1 is positioned to deliver the agent to specific target sites 30 in a patient. Device 10 may take the form of the like-numbered device shown in U.S. Pat. No. 4,692,147 (Duggan), assigned to Medtronic, Inc., Minneapolis, Minn. commercially available as the SynchroMed® infusion pump, which is incorporated by reference.

Figure 2:
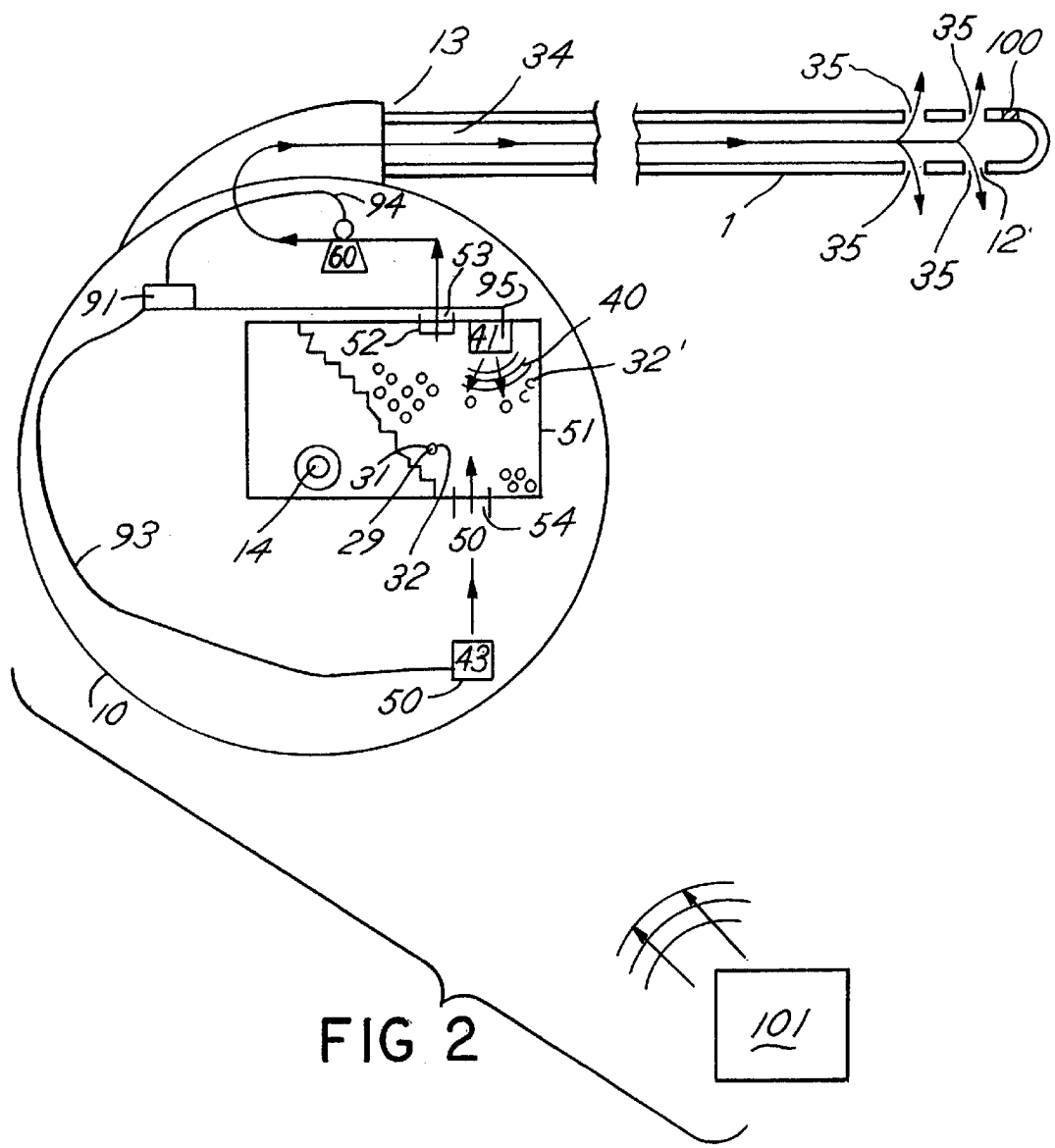
FIG. 2 is a diagrammatic illustration of a preferred embodiment of the present invention, including an electromechanical pump, microencapsulated drug in a reservoir, and a catheter.

As further shown in FIG. 2, drug 29 is maintained in capsule 31 by capsule wall 32. As shown in FIG. 2, capsule wall 32 can be broken by ultrasonic waves 40 emitted from an ultrasonic sound emitter 41. Broken capsule walls 32' are illustrated in FIG. 2. Once drug 29 is freed from capsule 31, it dissolves in a carrier fluid 50 in mixing tank reservoir 51. In a preferred embodiment, a filter 52 is placed at the outlet 53 of the reservoir 51. Filter 52 will allow drug 29 ions in the fluid 50 to exit the reservoir 51, but not permit the opened capsule 31 material to exit reservoir 51. Carrier fluid 50 is supplied to reservoir 51 through entry way 54. Carrier fluid 50 can be any suitable fluid, including bodily fluids.

In one preferred embodiment, the reservoir 51 can be emptied of capsule material, e.g., by accessing the reservoir 51 with a hypodermic needle through port 14. The empty capsule pieces will be small enough to pass through the hypodermic needle and removed from reservoir 51.

In another preferred embodiment, electromechanical pump 60 will pump the mixture of drug 29 and fluid 50 to catheter 1, where catheter 1 then conveys the mixture through proximal end 13 and lumen 34 of catheter 1, and through openings 35 at distal end 12 of catheter 1, to the target site 30 within the patient.

Device 10 is capable of changing the drug delivery of drug 29 based on reading from a sensor 100 measuring conditions at a target site 30 within the patient. Alternatively, device 10 can be programmed for drug delivery and/or drug delivery by device 10 can be changed from outside the patient via a telemetry unit 101 . By way of example, as shown in FIG. 2, device 10 can have an electrical control circuit 91 which controls ultrasonic sound emitter 41 via sound emitter control pathway 95 and the ultrasonic sound waves 40 therefrom. Those skilled in the art will recognize that electrical control circuit 91 can also control the flow of carrier fluid 50 to reservoir 51 via control carrier fluid pathway 93 and controlling carrier fluid metering device 43. Those skilled in the art will also recognize that electrical control circuit 91 can also control pump 60 via pump control pathway 94. Thus, electrical control circuit 91 can be used to control the pumping of the mixture of dissolved drug 29 and carrier fluid 50 to patient site 30 as desired.

It is contemplated that the above device and method for drug delivery will be able to permit drug delivery for about a one year period. In this embodiment, enough encapsulated drug would be stored in device 10 and last for the expected time period. At the end of that time period the implantable device 10 can be replenished via port 14 or explanted as desired.

As shown in FIG. 3, in another preferred embodiment, encapsulated drug 29 may be stored in a premixing vessel 71, and outside of reservoir 51. Drug 29 can be metered from premixing vessel 71 into reservoir 51 as needed via any suitable metering device 44. If more accurate drug infusion is required, a drug concentration sensor 90 can be placed in reservoir 51. Sensor 90 can send sensor signals via signal pathway 92 to an electrical control circuit 91 in device 10. The control circuit 91 controls drug metering device 44 via drug control signal pathway 45 so that drug metering device 44 only meters drug 29 into the reservoir 51 when the concentration of the drug 29 within reservoir 51 falls to a preset limit. The sensor 90 can also measure the concentration of drug 29 and electrical circuit 91 can control fluid metering device 43 via fluid control signal pathway 93 to precisely infuse into reservoir 51 the amount of carrier fluid 50 that is required to deliver a specified amount of drug 29 to the patient. In FIG. 3, encapsulated drug 29 can be provided to premixing vessel 71 through port 15. In this preferred embodiment port 14 is used only to remove broken capsules 32'.

By using the foregoing techniques, numerous drug delivery applications can be achieved to treat numerous conditions, including motor disorders, with a controlled degree of accuracy previously unattainable.

Further, in accordance with the present invention, reagents, which are used to produce a substance that can be measured by conventional sensors, can be replenished. A preferred embodiment is illustrated in FIG. 4. For example, an oxidase 400 can be contained within microcapsules 404, which are in turn contained in sensor reservoir 401. In this embodiment, a glucose containing fluid 402 from a target site is supplied to the sensor reservoir 401, wherein the glucose containing fluid 402 reacts with the oxidase 400 to produce oxygen. Sensor 403 can measure the oxygen produced, and since the amount of oxygen is directly proportional to the amount of glucose in the glucose containing fluid 402, the amount of glucose can be determined. Oxidase 400 can be supplied to sensor reservoir 401 in any suitable manner. As the oxidase in the sensor is consumed, additional oxidase can be freed from the microcapsules allowing the sensor to continue operation. As shown in FIG. 4 for example, microcapsules 404 containing oxidase 400 can be supplied by inserting a hypodermic needle (not shown) through the skin of the patient and through port 405 to supply oxidase 400 to the sensor reservoir 401. Further, as oxidase 400 is consumed in the reaction with glucose, it can be replenished as may be desired by inserting a hypodermic needle (not shown) through the skin of the patient and through port 405 to supply additional oxidase 400 to the sensor reservoir 401. Glucose containing fluid 402 from the target site can be supplied in any suitable manner. For example, the sensor 403 can be placed at a target site so that the glucose containing fluid 402 can flow through a semi-permeable membrane 406 and come into contact with the microcapsules 404 and thus oxidase 400 when freed from the microcapsules 404. As an alternative, glucose containing fluid 402 can be provided from the target site via a pump (not shown) to the sensor reservoir 401.

Those skilled in the art will also recognize that drug delivery in accordance with the present invention can be achieved by measuring the physiological conditions at the patient target site 30. For example, the measurement of hyperexcited cells can be detected with a sensor 100 as shown in FIGS. 2 and 3, or sensor 403 as shown in FIG. 4. Further, sensor 100 can send a signal to electrical control circuit 91, which as shown in FIG. 3 as an example, controls the mixing of drug 29 and carrier fluid 50. The sensor 403 shown in FIG. 4 can also be used to send a signal to an electrical control circuit 91, which in turn can regulate drug delivery from an implantable drug delivery device, including those shown in FIGS. 2 and 3.

Those skilled in the art will recognize that the capsules can be broken in any suitable manner, including: ultrasonic waves, mechanical crushing or grinding; chemically dissolving or splitting; applying an electrical current to potentiate a chemical reaction; heating; or applying pressure (e.g. hydrostatic pressure).

Those skilled in that art will recognize that the preferred embodiments may be altered or amended without departing from the true spirit and scope of the invention, as defined in the accompanying claims.

We claim:

1. An implantable drug delivery device comprising:
    a microencapsulated drug contained within at least one capsule,
    a carrier fluid that will dissolve the drug when freed from the capsule,
    a drug releaser for freeing the microencapsulated drug from the capsule,
    a reservoir in which the carrier fluid dissolves the drug, and
    an electromechanical pump to convey the dissolved drug to a catheter, through which the drug is delivered.

2. The device of claim 1, wherein the drug releaser for freeing the microencapsulated drug from the capsule comprises an ultrasonic sound emitter that emits sufficient sound waves to break the capsule open.

3. The device of claim 1, wherein the drug releaser for freeing the microencapsulated drug from the capsule comprises a mechanical crushing or grinding device that exerts sufficient force to break the capsule open.

4. The device of claim 1, wherein the drug releaser for freeing the microencapsulated drug from the capsule comprises a chemical dissolving or chemical splitting apparatus to break the capsule open.

5. The device of claim 1, wherein the drug releaser for freeing the microencapsulated drug from the capsule comprises an electrical current emitter to potentiate a chemical reaction in the capsule sufficient to break the capsule open.

6. The device of claim 1, wherein the drug releaser for freeing the microencapsulated drug from the capsule comprises a heater that conveys sufficient heat to the capsule to break the capsule open.

7. The device of claim 1, wherein the drug releaser for freeing the microencapsulated drug from the capsule comprises a pressure device that exerts sufficient pressure on the capsule to break the capsule open.

8. The device of claim 1, wherein the device further has a sensor that senses the physiological conditions at a target site.

9. The device of claim 1, wherein the device is programmed for drug delivery to a target site.

10. The device of claim 1, wherein the device is programmed for drug delivery to a target site via telemetry.

11. The device of claim 8, wherein the device has an electrical control circuit that receives signals from the sensor and controls the drug releaser for freeing the microencapsulated drug from the capsule based on the sensor signals.

12. The device of claim 8, wherein the device has an electrical control circuit that receives signals from the sensor and controls the amount of the drug delivered based on the sensor signals.

13. The device of claim 8, wherein the device has a control drug releaser responsive to the sensor signal for regulating a therapeutic dosage of the drug to the target site.

14. The device of claim 1, wherein the device further has a premixing vessel that contains the microencapsulated drug which delivers the microencapsulated drug to the reservoir for mixing with the carrier fluid.

15. A method for drug delivery by an implantable electromechanical pump and a catheter having a discharge portion and having a proximal end coupled to said pump, said method comprising the steps of:
    implanting said pump outside a patient site;
    surgically implanting said catheter so that said discharge portion lies adjacent a predetermined infusion site in the patient;
    supplying to a reservoir at least one capsule containing a drug;
    supplying to the reservoir a carrier fluid capable of dissolving the drug;
    breaking open the capsule so as to free the drug from the capsule;
    dissolving the drug in the carrier fluid to form a mixture;
    and pumping the mixture to and through the discharge portion of the catheter and to the infusion site.

16. The method of claim 15, wherein the step of breaking open the capsule so as to free the drug from the capsule comprises subjecting the capsule to sound waves sufficient to break open the capsule.

17. The method of claim 15, wherein the step of breaking open the capsule so as to free the drug from the capsule comprises subjecting the capsule to a mechanical force sufficient to break open the capsule.

18. The method of claim 15, wherein the step of breaking open the capsule so as to free the drug from the capsule comprises subjecting the capsule to a chemical sufficient to dissolve or split the capsule in a sufficient manner to break open the capsule.

19. The method of claim 15, wherein the step of breaking open the capsule so as to fee the drug from the capsule comprises subjecting the capsule to an electrical current to potentiate a chemical reaction in the capsule sufficient to break the capsule open.

20. The method of claim 15, wherein the step of breaking open the capsule so as to free the drug from the capsule comprises subjecting the capsule to heat sufficient to break the capsule open.

21. The method of claim 15, wherein the step of breaking open the capsule so as to free the drug from the capsule comprises subjecting the capsule to pressure sufficient to break the capsule open.

22. The method of claim 15, wherein the method has the further step of sensing a physiological condition at the infusion site.

23. The method of claim 15, wherein the method has the further step of sensing an amount of a substance related to a physiological condition at the infusion site.

24. The method of claim 22, wherein the method has the further step of controlling the amount of drug delivery to the infusion site based on the physiological condition sensed at the infusion site.

25. The method of claim 23, wherein the method has the further step of controlling the amount of drug delivery to the infusion site based on the amount of the substance sensed at the infusion site.

26. The method of claim 15, wherein the method has the further step of programming an electrical circuit to control the amount of drug delivery to the infusion site.

27. The method of claim 15, wherein the method has the further step of programming an electrical circuit via telemetry to control the amount of drug delivery to the infusion site.

28. The method of claim 15, having the additional step of removing capsules that have been broken open, and replenishing the reservoir with at least one new capsule containing a drug through a port in the reservoir.

29. The method of claim 15, having the additional step of controlling the delivery of the drug to the infusion site based on a measurement of the concentration of the drug within the carrier fluid.

30. The method of claim 15, having the additional steps of implanting in the patient a premixing vessel containing the capsulated drug, and supplying the capsulated drug to the reservoir from the premixing vessel.

31. An implantable reagent delivery and sensor device comprising:

a microencapsulated reagent contained within at least one capsule, a sensor having a reservoir that contains the microencapsulated reagent, a drug releaser for freeing the microencapsulated reagent from the capsule, the freed reagent being capable of reacting with a first substance to produce a second substance that is directly proportional to the amount of the first substance, the sensor capable of measuring the amount of the second substance.

32. The implantable reagent delivery and sensor device of claim 31, wherein the reagent is an oxidase, the first substance is oxygen, and the second substance is glucose, and the sensor is a glucose sensor.

33. The implantable reagent delivery and sensor device of claim 31, further having a transfer port in the reservoir through which capsules that have been broken open can be removed from the reservoir and microencapsulated reagent can be supplied to the reservoir.

34. The implantable reagent delivery and sensor device of claim 31, wherein the device is electrically connected to an electrical circuit that controls a delivery of a drug to an infusion site based on the measurement of the second substance produced by the reaction of the first substance with the reagent.

* * * * *

UNITED STATES PATENT AND TRADEMARK OFFICE
CERTIFICATE OF CORRECTION

PATENT NO.     : 6,458,118 B1
DATED          : October 1, 2002
INVENTOR(S)    : Lent et al.

Page 1 of 1

It is certified that error appears in the above-identified patent and that said Letters Patent is hereby corrected as shown below:

<u>Column 6,</u>
Line 46, delete the word "fee" and substitute therefor -- free --.

Signed and Sealed this

Twenty-fifth Day of February, 2003

JAMES E. ROGAN
*Director of the United States Patent and Trademark Office*